United States Patent [19]
Scher et al.

[11] Patent Number: 5,562,914
[45] Date of Patent: Oct. 8, 1996

[54] IMPREGNATED POROUS GRANULES AND A POLYURETHANE MATRIX HELD WITHIN THE PORES THEREOF AND HOLDING A LIQUID MATERIAL FOR CONTROLLED RELEASE OF LIQUID MATERIAL AND PROCESS THEREFOR

[75] Inventors: Herbert B. Scher, Moraga; Marius Rodson, El Sobrante, both of Calif.

[73] Assignee: Zeneca Inc., Wilmington, Del.

[21] Appl. No.: 624,152

[22] Filed: Dec. 6, 1990

[51] Int. Cl.$^6$ .................................... A01N 25/08
[52] U.S. Cl. .................. 424/408; 424/409; 424/484; 424/486
[58] Field of Search .................... 424/484, 486, 424/408, 409, 489, 490, 497; 514/949, 951; 71/64.11, 64.13, 904

[56] References Cited

U.S. PATENT DOCUMENTS

| | | | |
|---|---|---|---|
| 3,074,845 | 1/1963 | Geary | 424/419 |
| 4,118,218 | 10/1978 | Drewe et al. | 71/92 |
| 4,223,070 | 9/1980 | Hahn et al. | 428/407 |
| 4,230,809 | 10/1980 | Heinrich et al. | 521/65 |
| 4,280,833 | 7/1981 | Beestman et al. | 71/100 |
| 4,283,325 | 8/1981 | Berthet et al. | 524/90 |
| 4,681,806 | 7/1987 | Matkan et al. | 428/402.21 |
| 4,743,448 | 5/1988 | Bahadir et al. | 424/405 |
| 4,746,513 | 5/1988 | Smith | 424/408 |
| 4,772,490 | 9/1988 | Kogler et al. | |
| 4,874,422 | 10/1989 | Woolard | 71/95 |
| 4,898,734 | 2/1990 | Mathiowitz et al. | 424/426 |
| 4,940,588 | 7/1990 | Sparks et al. | 424/490 |
| 5,028,435 | 7/1991 | Katz et al. | 424/484 |
| 5,034,222 | 7/1991 | Kellett et al. | 424/76.4 |
| 5,047,243 | 9/1991 | Antfang et al. | 424/408 |
| 5,064,653 | 11/1991 | Sessions et al. | 424/445 |
| 5,326,573 | 7/1994 | Antfang et al. | 424/490 |

FOREIGN PATENT DOCUMENTS

| | | |
|---|---|---|
| 0005302 | 11/1979 | European Pat. Off. . |
| 2007095 | 9/1977 | United Kingdom . |

*Primary Examiner*—John C. Bleutge
*Assistant Examiner*—Robert H. Harrison
*Attorney, Agent, or Firm*—Joel G. Ackerman; William E. Dickheiser; Edwin H. Baker

[57] ABSTRACT

A composition of matter having a clay porous granule and a polyurethane matrix formed from the polymerization of a polyol and a polyisocyanate and held within the pores of the granule and having uniformly distributed throughout the polyurethane matrix a liquid material, for example, a pesticide and a method for loading a porous granule with the polyurethane and the liquid material by:

(a) spraying a porous granule with a liquid composition comprising a polyol, a polyisocyanate and a liquid material to be retained in the porous granule, and (b) polymerizing the polyol and the polyisocyanate to form a polyurethane matrix polymer which has the liquid materials uniformly distributed throughout the polyurethane matrix.

4 Claims, No Drawings

IMPREGNATED POROUS GRANULES AND A POLYURETHANE MATRIX HELD WITHIN THE PORES THEREOF AND HOLDING A LIQUID MATERIAL FOR CONTROLLED RELEASE OF LIQUID MATERIAL AND PROCESS THEREFOR

BACKGROUND OF THE INVENTION

This invention relates to impregnated granules. In particular, this invention relates to porous granules containing liquid material held therein for controlled release by a polyurethane matrix.

The invention further relates to a process for preparing such impregnated granules. The effect of the impregnation is to control the rate of release of a liquid material, e.g. a liquid pesticide material to the surrounding environment where applied. The impregnation thus serves to increase the effectiveness and the useful life of the liquid contained in the treated granules. By limiting the maximum rate of diffusion of the liquid material from the pores, the polyurethane matrix helps to prevent the usual occurrence of a rapid and excessive initial release.

The use of membranes, coating, and capsules for the controlled release of liquid materials is well known in the art of both agricultural and non-agricultural chemicals. In the agricultural area, such controlled release techniques have improved the efficiency of herbicides, insecticides, fungicides, bactericides, and fertilizers, coating technology for agricultural uses include coated droplets, such as microcapsules, coated solids such as porous or non-porous particles, and coated aggregates of solid particles. Non-agricultural uses include encapsulated dyes, inks, pharmaceuticals, flavoring agents, and fragrances.

Many prior art coatings completely enclose the material held inside, and prevent any release of the material until the coating is broken, dissolved, or otherwise removed. There is a need in the agricultural industry for a granular product containing a pesticide material that allows the controlled release of the entrapped pesticide material to the surrounding medium.

Porous granules of this invention offer distinct advantages for the application of chemicals in a wide variety of commercial applications by improving the ease of handling as well as the ease of distributing or dispersing the chemicals over a wide area, and by offering controlled release characteristics. In addition, porous granules of high pore volume are capable of retaining a considerable volume of liquid inside their pore structure, with only a small fraction of liquid initially exposed to the outer surroundings.

It is therefore an object of this invention to provide a process for the preparation of porous granules impregnated with a liquid material and to provide for a polyurethane matrix which permits the uniform distribution of the liquid material inside the porous structure of the granules and provides for a controlled rate of release of the liquid material.

Another object of this invention is to provide a novel composition of matter of an impregnated granule with the pore structure uniformly filled with a polyurethane polymer that is capable of providing a controlled rate of release of the liquid contained in the structure of the polyurethane material.

SUMMARY AND BRIEF DESCRIPTION OF THE INVENTION

According to the present invention, it has been discovered that pores of a porous granule can be efficiently and uniformly filled with a polyurethane having distributed therein a liquid material, especially a pesticide material. Upon contact of these filled granules with water or moist soil the held liquid material will diffuse from the polyurethane matrix at a controlled rate. Also, this invention relates to a method for impregnating a porous granule with monomers that form a polyurethane material which is at least partially swellable when in contact with water. A liquid material is held within the form polyurethane which is held within the pores of a granule by adding to the porous granules a polymerizable mixture of monomers for preparing a polyurethane and a liquid material.

The method of this invention comprises the steps of loading a porous granule with a mixture of a liquid isocyanate monomer and a liquid glycol monomer which mixture polymerizes to form a polyurethane polymer and a liquid material to be held therein.

The method and composition of matter of the present invention are characterized by the fact that the polyurethane polymer matrix is formed in situ in the porous structure of a porous granule. According to this invention, the reactant monomers and the liquid material to be held are sprayed onto the surface of the porous granules. The process of this invention involves impregnating the pores of granules whereby all ingredients required for formation of the polyurethane are first mixed together along with the liquid material to be held as a common body of fluid which is then sprayed onto the granule in a single application.

According to the present invention, the above mixture is sprayed onto the surface of the granule and allowed to penetrate within the pores of the porous granules. After application the following chemical reaction takes place:

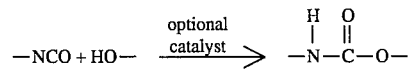

The polyisocyanate monomer is represented by the symbol (—NCO) and the polyol monomer is represented by the symbol (HO—).

The rate determining step in the above sequence is the reaction time between the polyisocyanate and polyol to form the urethane linkage.

DETAILED DESCRIPTION OF THE INVENTION

The porous granular material to be used in the practice of the present invention is any porous granular solid substance which is insoluble in and inert to any of the monomers or liquid materials used in the practice of this invention. Porous granules formed by extrusion, agglomeration, or prilling are useful in the present invention as well as materials in their naturally occurring form. Naturally occurring porous granules can be subjected to physical modification prior to use, such as drying, crushing, and screening, to achieve the desired size and moisture characteristics. In general, the granule size can range from under 1 millimeter to over 1 centimeter in diameter or length. In agricultural usage, a typical granule size is about 1 to 2 millimeters in diameter. Examples of such granular materials are vermiculite, sintered clay granules, kaolin, attapulgite clay, montmorillonite clay, and silica.

In addition to liquid materials, solid materials can also be held by the composition of this invention. However, they must be dissolved in a solvent thereto. Any inert solvent which will dissolve the solid material will be suitable, particularly aliphatic compounds, aromatic compounds, or their halogenated derivatives. Examples of solvents useful for this purpose include heptane, octane, benzene, toluene, xylene, mesitylene, methylene chloride, 1,2-dichloroethane, and chlorobenzene.

The polyurethane matrix useful in the practice of this invention is prepared from two components: a polyol and a polyisocyanate. It is prepared by mixing the polyisocyanate monomer and the polyol monomer with the pesticide liquid immediately before the spraying of the combination onto the porous granules.

After mixing, the polyisocyanate and the polyol react immediately, resulting in continual viscosity buildup and eventual gelation.

Thus, the combined polyisocyanate and polyol monomers with pesticide liquid must be quickly mixed to form a homogenous mixture. The resulting mixture must be quickly sprayed onto the surface of the porous granule substrate.

Various types of conventional mixing equipment are useful in the practice of this invention. Preferably, the mixing is done in a conventional static type mixer. The liquid polyol and the liquid polyisocyanate monomers with pesticide liquid are pumped into one end of the static mixer and the mixed components are forced from an orifice at the other end of the mixer.

Preferably, the residence time in the screw-mixer is less than about 5 seconds.

The resulting mixture of the polyisocyanate, polyol and liquid material is immediately sprayed onto the surface of the porous granules by conventional spraying equipment.

The preferred liquid pesticide material of this invention is not limited to any particular class of compounds. The compounds can be liquid or solids. Preferably, the pesticide is liquid and is unreactive with either the polyol or polyisocyanate monomers of this invention.

In the practice of this invention, the liquid pesticide material must be mixed with either one or both the polyisocyanate or polyol monomers. Preferably about equal amounts of the liquid pesticide component are mixed separately with both the polyol and the polyisocyanate.

The individual mixtures of (a) liquid pesticide and liquid polyol monomer and (b) liquid pesticide and liquid polyisocyanate monomer quickly are mixed uniformly before spraying the resulting three-component mixture of polyol, polyisocyanate and pesticide onto the surface of porous granules.

The urethane polymers of this invention are very well known by those skilled in the art. They are described in numerous publications, including Kirk-Offmer Encyclopedia of Chemical Technology, 3rd edition, volume 23, pages 576–608 and Kirk-Offmer Encyclopedia of Polymer and Science Engineering, volume 13, pages 243–303, 1988 which are incorporated herein by reference.

As stated previously, urethane polymers are formed by the condensation polymerization of polyisocyanate and a polyol.

The polyols are described in many texts, including SRI International Report No. 45A, entitled "Polyols for Making Polyurethanes" which is incorporated herein by reference.

Organic polyisocyanates which can be used in the present invention are well-known by those skilled in the art and include conventional aliphatic, alicyclic, and aromatic polyisocyanates. Aromatic polyisocyanates are preferred. Examples of suitable polyisocyanates are:

hexamethylene-1,6-diisocyanate
1-chloro-2,4-phenylene diisocyanate
m-phenylene diisocyanate
p-phenylene diisocyanate
4,4'-methylene-bis(phenyl isocyanate)
2,4-toluene diisocyanate
2,6-toluene diisocyanate
3,3'-dimethyl-4,4'-biphenylene diisocyanate
4,4'-methylene bis(2-methylphenyl isocyanate)
3,3'-dimethoxy-4,4'-biphenylene diisocyanate
2,2',5,5'-tetramethyl-4,4'-biphenylene diisocyanate
1,5-naphthalene diisocyanate, Polymeric isocyanates such as polymethylene polyphenylisocyanates can also be used. Several types are sold under the trade names "Mondur MRS®" (Mobay Chemical Company) and "PAPI®" (Dow Chemical Company). Some of the above-mentioned polyisocyanates have shown particular efficacy when used in combinations of two or more. One such example is an 80:20 weight percent blend of the 2,4- and 2,6-isomers of toluene diisocyanate. This combination is commercially available under trade names such as "Hylene TM®" (E. I. Depont de Nemours & Co., Inc.), "Nacconate 80®" (Allied Chemical Corporation), and "Mondur TD-80®" (Mobay Chemical Company).

The term "polyisocyanate" is intended to include any organic molecule containing two or more isocyanate (—N=C=O) groups. When three or more such groups or two groups plus a third reactive group are present on one molecule, cross-linking of this molecule with other polyfunctional groups or other molecules can occur. The resulting cross-linked structure is particularly rigid.

Examples of polyisocyanate compounds useful in the practice of this invention to prepare the polyurethane polymers are as follows:

tolylene diisocyanate (TDI)
polymethylene polyphenyl isocyanate (PAPI)
diphenyl methane-4,4' diisocyanate (MDI)
halogenated MDI
hexylmethylene diisocyanate
isophorone diisocyanate
naphthalene 1,5 diisocyanate
3,3-ditoluene-4,4'-diisocyanate (TODI), The polyols that are most useful in the practice of this invention are those used to manufacture elastomers, adhesives or sealants. Generally, these have large chains and are well known to those skilled in the art. They are described in numerous publications and patents including *Polyols for Making Polyurethanes*, Supplement A, Report No. 45A by SRI International, Menlo Park, Calif., May, 1982 which is incorporated herein by reference.

Polyols useful for making polyurethanes can be classified into three chemical classes: (1) polyether polyols that contain ether linkages in a straight or branched chained hydrocarbon backbone with hydroxyl end groups, (2) polyester polyols with ester linkages and (3) polyols having neither ether linkages nor ester linkages but only hydrocarbon chains.

The hydrophilicity/hydrophobicity of the prepared polyurethane component of this invention can be varied by varying the ratio of ethylene oxide to propylene oxide in the polyether type polyols. The greater the amount of ethylene oxide, the greater the hydrophilicity of the prepared polyurethane.

The polyether type polyols are well known to those skilled in the art and are made from glycerol and an alkylene oxide.

The polyether polyol which is most preferred is made from glycerol and an alkylene oxide. The alkylene oxide is propylene oxide, or propylene oxide and a small percentage of ethylene oxide, with the two alkylene oxides being either mixed and added together, or added separately and successively. By varying the amount, ratio, and order of addition of the alkylene oxides, one obtains different grades of polyols with different performance characteristics.

It will be apparent to one of ordinary skill in the art that the diffusion properties of the liquid material held in the polyurethane matrix will be determined by the chemical composition of the polyurethane.

Catalysts can also be used in the practice of this invention to accelerate the polymerization. Catalysts suitable for use in the present invention are basic organic tertiary amines and alkyl tin carboxylates. Included among such amines are monoamines and polyamines, as well as amine containing further non-carbon atoms such as oxygen. Examples of tertiary amines useful in the present invention are:

triethylamine
triethylenediamine
tri-n-butylamine
thrimethylamine
N-methylmorpholine,
N,N'-tetramethyl-1,3-butanediamine, Examples of alkyl tin carboxylates with are useful as catalysts in the present invention are:

dibutyltin diacetate
tributyltin acetate
dibutyltin dilaurate
dibutyltin laurate
dibutyltin maleate
dibutyltin laurate maleate
dibutyltin-bis(6-methylaminocarpoate).

The amount of catalyst which will constitute a catalytic amount and thus be useful to the process of the invention will be apparent to one of ordinary skill in the art as any amount which increases the rate of reaction between the polyol and the polyisocyanate. The extent of catalytic effect will vary with the particular polyisocyanate used, the concentration of the polyisocyanate, and the temperature of the monomers used during the application process. More reactive polyisocyanates and higher temperatures will diminish the quantity of catalyst required. Thus, there is no critical amount of catalyst concentration. Generally, however, it will be most convenient to use a catalyst concentration of between about 0.1% and about 10% by weight of the weight of the polyisocyanate. Preferably, the catalyst concentration will range from about 0.05% to about 5% by weight.

A wide variety of liquid materials can be held in the polyurethane matrix by the process of the present invention. The most useful liquids are those which do not react with polyisocyanate or polyol monomers, or any of the catalysts contemplated for use in the present invention. Any non-reactive liquid material which will diffuse through the polyurethane matrix is suitable. The held liquid material will diffuse out into water, moist soil, or any other aqueous surrounding medium.

Suitable pesticide components to be held include herbicides, insecticides, fungicides, hematocides, bactericides, rodenticides, moluscides, acaricides, larvacides, animal, insect, and bird repellents, plant growth regulators, fertilizers, pheromones, sex lures and attractants, and flavor and odor compositions. Examples of herbicides include the following:

1. Anilides

Alachlor—2-chloro-2',6'-diethyl-N-(methoxymethyl)acetanilide
Metolachlor—2-chloro-N-(2-ethyl-6-methylphenyl)-N-(2-methoxy-1-methylethyl)acetamide
Propanil—N-(3,4-dichlorophenyl)propionanilide 2. Triazines Atrazine—2-chloro-4-(ethylamino)-6-isopropylamino)-s-triazine
Cyanazine—2-chloro-4-(1-cyano-1-methylethylamino)-6-ethylamino—s—triazine
Metribuzin—4-amino-6-tert-butyl-3-(methylthio)-1,2,4-triazin-5(4H)-one 3. Thiocarbamates Molinate—S-ethyl hexahydro-1H-azepine-1-carbothioate
Butylate—S-ethyl diisobutylthiocarbamate 4. Ureas Monuron—3-(p-chlorophenyl)-1,1-dimethylurea
Linuron—3-(3,4-dichlorophenyl)-1-methoxy-1-methylurea 5. Toluidines Trifluralin—α,α, α-trifluoro-2,6-dinitro-N,N-dipropyl-p-toluidine
Pendimethalin—N-(1-ethylpropyl)-3,4-dimethyl-2,6-dinitrobenzeneamine 6. Hormones 2,4-D-(2,4-dichlorophenoxy) acetic acid
MCPA—(2-methyl-4-chlorophenoxy) acetic acid 7. Diazines Bentazon—3-isopropyl-1H-2,3,1-benzothiadiazin-4 (3H)-one 2,2-dioxide
Oxadiazon—2 -tert-butyl-4-(2,4 -dichloro-5-isopropoxyphenyl) -$\Delta^2$—1,3,4-oxadiazolin-5-one 8. Diphenyl ethers Acifluorfen—sodium 5-[2-chloro-4-(trifluoromethyl)phenoxy]-2-nitrobenzoate
Fluazifop-butyl—(±)-butyl 2-[4[(5-(trifluoromethyl)-2-pyridinyl)oxy]phenoxy]propanoate
Chlomethoxynil—2,4-dichlorophenyl 3-methoxy-4-nitrophenyl ether 9. Imidazolinones Imazaquin—2-[4,5-dihydro-4-methyl-4-(1-methylethyl)-5-oxo-1H-imidazol-2-yl]-3-quinolin carboxylic acid 10. Sulfonyl ureas Bensulfuron methyl—methyl 2-[[[[[(4,6-dimethoxypyrimidin-2-yl)amino]carbonyl]amino]sulfonyl]methyl] benzoate
Chlorimuron ethyl—ethyl 2-(((((4-chloro-6-methoxypyrimidin-2-yl)amino)carbonyl)amino)sulfonyl)benzoate 11. 2-(2-Substituted benzoyl)-1,3-cyclohexanediones 2-(2'-chloro-4-methysulfonyl benzoyl)-1,3-cyclohexanedione 12. Miscellaneous compounds Dimethazone—2-(2-chlorophenyl)methyl-4,4-dimethyl-3-isoxazolidinone
Norflurazon—4-chloro-5-(methylamino)-2-α,α,α-trifluoro-m-tolyl)-3-(2H)-pyridazinone
Dalapon—2,2-dichloropropionic acid
Glyphosate—isopropyl amine salt of N-(phosphonomethyl) glycine
Fenoxaprop-ethyl—(+)-ethyl-2,4-((6-chloro-2-benzoxazoloxy)phenoxy)propanoate Examples of insecticides include:

O-ethyl-S-phenylethyl phosphonidithioate,

S-(1,2-dicarbethoxyethyl)-O,O-dimethyl dithiophosphate, methyl O,O -dimethyl-o,p-nitrophenyl phosphorothioate, 1,1,1-trichloro-2,2-bis(p-chlorophenyl), and 2,3-dihydro-2,2-dimethyl-7-benzofuranyl methyl carbamate.

Sex lures and attractants include methyl 4-allyl-2-methoxyphenol and tertiary butyl 4-chloro-2-methyl cyclohexane carboxylate. For comprehensive lists of suitable pesticide compositions see O. Johnson *Chemical Week*, pp. 29–64, Jun. 21, 1972. Other compositions suitable for use in accordance with the invention will be known to those skilled in the art.

While there is no critical amount of the 3-component mixture of pesticide, polyol and polyisocyanate that is sprayed onto the porous granules, it will be apparent to those skilled in the art that once the pores are filled, further addition of the 3-component mixture will not be retained by the granules. Thus, the process of the invention is most efficiently operated when a quantity of the sprayed 3-component mixture is approximately equal to the available pore volume of the granules. The actual, pore volume can be determined by oil absorptivity measurements or by such analytical techniques as nitrogen or mercury porosimetry.

While the temperature at which the process of the present invention can be performed is not critical, it will be most convenient to spray the 3-component mixture at approximately ambient temperature, about 15° C. to about 30° C. In general, however, the rate of polymerization reaction can be increased by increasing the temperature after spraying. The upper temperature limit will be determined by such considerations as stability of the material to be held in the polyurethane matrix and loss of any liquid material by vaporization. Temperatures close to room temperature are particularly preferred when toxic system components are used. Such toxic substances may be either the liquid material to be held or the polyisocyanate monomer.

Specific examples are set forth below showing the preparation of sprayed granule according to the process of the present invention, and the resulting slow-release effects. These examples are included for illustrative purposes only, and are not intended to be interpreted as imposing any limitations on the scope of the invention.

EXAMPLE I 78.77 grams (g) porous clay granules, Attaclay 20/40 (granule size between 20 and 40 U.S. mesh), were placed in a 500 milliliter (ml) stainless steel beaker that was mounted to a shaft which was coupled to an electric motor. The beaker was rotated at an angle of about 45 degrees to the horizon at about 100 revolutions per minute (r.p.m.).

The mixture of 7.20 grams of polymethylene polyphenyl isocyanate, PAPI 135 a polyisocyanate compound sold by Dow Chemical Company having an average of three isocyanate groups and having the structural formula $$OCN-\phi-CH_2-[\phi(NCO)-CH_2-]_n-\phi-NCO$$

$(n_{avg} = 1)$ 3.40 grams 1,5 pentanediol and 10.63 grams S-ethyl diisobutylthiocarbamate were mixed together by shaking a few seconds in a 3 ounce (oz.) narrow mouth bottle capped with the atomizer head from a DeVilbiss Model 15 Sprayer.

High pressure air was used to pull the liquid from the bottle and atomize it as a fine mist.

The mist was sprayed onto the surface of the rotating clay granules.

The polyol and isocyanate monomers gradually polymerized inside the pores of the clay over a period of several hours, entrapping the liquid thiocarbamate herbicide compound.

A control sample was prepared in a similar manner except that only the thiocarbamate was sprayed onto the porous clay.

Wet Soil Bioassay Test

Aluminum test flats (7"×9"×3" deep) filled with sterile Keaton loamy sand soil containing fertilizer were moistened with water on the day of treatment. Enough loaded granules from Example I were hand spread on the surface of the wetted soil to give an application rate of 2 or 4 pounds thiocarbamate per acre.

One set of test flats was watered immediately after application of the granules and another set was watered 24 hours after application of the granules.

Pre-emergence Herbicide Test

The seeds of five different weed species were planted in the loamy sand soil in individual rows using one species per row across the width of a flat. The weeds used were (1) green foxtail (FT) (*Setaria Viridis*) (2) watergrass (WG) (*Echinochloa crusgalli*), (3) shattercane (SHC) (*Sorghym bicolor*), (4) wild oat (WO) (*Avena fatua*), and (5) yellow nutsedge (YNG) (*Cyperus esculentus*). Ample seeds were planted to give about 20 to 40 seedling per row, after emergence, depending upon the size of the plants.

After treatment and seeding, the flats were placed in the greenhouse at a temperature of 70° to 80° F. and watered by sprinkling. Two weeks after treatment, the degree of injury or control was determined by comparison with untreated check plants of the same age. Average injury rating from 0 to 100% was recorded for five weed species as percent control with 0% representing no injury and 100% representing complete control.

The results of the test are shown in the following table. (Thiocarbamate applied at 4 lb/A).

|  | Percent Weed Control Watered at | |
| --- | --- | --- |
|  | 0 hours | 24 hours |
| Clay Granule with thiocarbamate trapped in polyurethane matrix | 72 | 35 |
| Clay Granule with thiocarbamate | 77 | 4 |

As can be seen, the polyurethane matrix of Example I was effective in reducing evaporation of the thiocarbamate from the wet soil surface during the 24 hour interval.

EXAMPLE II 79.7 g porous montmorillonite clay granyles, Agsorb 24/48 (granule size between 24 and 48 U.S. mesh) were placed in a 500 ml stainless steel beaker that was mounted at the bottom to the shaft of an electric motor. The beaker was rotated at an angle of about 45 degrees to the horizon at about 100 r.p.m.

A mixture of 7.9 g s,s-di-tertiary butyl ethylphosphonotrithioate (a liquid insecticidal compound), 2.0g xylene solvent, 8.4g Pluronic® L31 polyol sold by BASF having the structural formula $HO-(CH_2CH_2O)_x-(C(CH_3)H-CH_2O)_y-(CH_2CH_2)_z-H$ where the ratio of Y/X+Z is about 9:1 and the molecular weight (m.w.) of the polyoxypropylene moiety is about 950 and the average total m.w. of the monomer is about 1100 with a Brookfield viscosity of 165 cps measured at 25° C. and a specific gravity (s.g.) of 1.02 measured at 25° C., 2.0 g PAPI 135 were mixed together by shaking a few seconds in a 302 narrow mouth bottle capped with the atomizer head from a DeVilbiss Model 15 atomizer.

High pressure air was used to pull the liquid from the bottle and atomize it as a fine mist onto the surface of the rotating clay granules.

The polyol and isocyanate monomers gradually polymerized inside the pores of the clay over a period of several hours, entrapping the liquid insecticide compound.

EXAMPLE III

A control sample was prepared similar to that of Example II except no polyol or isocyanate monomers were used in the mixture that was sprayed onto the surface of the montmorillonite clay. Dipropylene glycol (8.37 percent) was used to stabilize the insecticidal compound from deactivation by the clay. Otherwise, the ingredients for the mixture were the same.

The products of Examples II and Examples III were tested for soil insecticidal usefulness according to the following test procedure:

Procedure for Evaluating Phytotoxicity of Soil Insecticides to Corn

Corn seeds were planted in aluminum pans at a rate of 10 seeds per 12 inch row times four rows per pan. Treatments were made by metering out the granules directly into the seed furrow. Rates were calculated on the basis of 34 mg. of active ingredient per 12 inches of row equaling 1.0 round of active ingredient per acre. Observations made included: % germination at n days after planting, type and extent of injury, and mean heights of plants.

Residual soil assay on western spotted cucumber beetle larvae/eggs (*Diabrotica undecimpunctata undecimpunctata*): Test compounds were diluted in acetone and pipetted into 10 round plastic tubs with 900 g dry sandy loam soil. The compound was incorporated with vigorous shaking. 100 ml of deionized water was added and the tubs were covered with plastic lids and stored at 78° F. 10 gram samples of the treated soil were removed at weekly intervals and placed in 1 oz. plastic cups with 0.2 ml dacagin solution with approximately 50 western spotted cucumber beetle eggs. A piece of romaine lettuce was added 3 to 4 days later. Seven to 9 days later, the lettuce was rated for larval feeding. For granular formulations: same except the granules of compounds are incorporated into soil instead of technical materials in acetone.

The results of the testing appear below.

| Phytotoxicity and Efficacy of SC0882 Granule Formulations | | | |
|---|---|---|---|
| Formulation | SC0882 Rate (lb/A) | Corn Injury* | LC-50 (ppm)** |
| As Example II (Contains Polyurethane Matrix) | 1 10 | None Light Burn | <0.1 |
| As Example III (No Polyurethane Matrix) | 1 10 | None Moderate Burn | 0.1 |

*Corn Injury Scale: None Light Burn Moderate Burn Severe Burn
**Western Spotted Cucumber Beetle (Diabrotica)

The formulation with the polyurethane matrix displayed higher insecticidal activity and at the same time showed less corn phytotoxicity,

We claim:

1. A composition of matter comprising (a) a porous granule having a diameter of between 48 U.S. mesh and 1 centimeter and (b) a polyurethane matrix held within the pores of the granule and having uniformly distributed throughout the polyurethane matrix a liquid material which will diffuse through the polyurethane matrix.

2. The composition of claim 1 wherein the liquid material is a pesticide.

3. The composition of claim 1 wherein the liquid material is a pesticide and the polyurethane matrix is formed from the polymerization of a polyol and a polyisocyanate.

4. The composition of claim 1 wherein the granule is clay, the liquid material is a pesticide and the polyurethane matrix is formed from the polymerization of a polyol and a polyisocyanate.

* * * * *